(12) United States Patent
Weinreich et al.

(10) Patent No.: US 6,440,336 B1
(45) Date of Patent: Aug. 27, 2002

(54) METHOD FOR PRODUCING A POWDER PRODUCT FROM A LIQUID SUBSTANCE OR MIXTURE OF SUBSTANCES

(75) Inventors: Bernd Weinreich, Tutzing; Rudolf Steiner; Eckhard Weidner, both of Erlangen; Johann Dirscherl, Kulmbach, all of (DE)

(73) Assignee: Adalbert-Raps-Stiftung (DE)

( * ) Notice: Subject to any disclaimer, the term of this patent is extended or adjusted under 35 U.S.C. 154(b) by 0 days.

(21) Appl. No.: 09/529,041
(22) PCT Filed: Oct. 6, 1997
(86) PCT No.: PCT/EP97/05484
§ 371 (c)(1),
(2), (4) Date: Jun. 16, 2000
(87) PCT Pub. No.: WO99/17868
PCT Pub. Date: Apr. 15, 1999
(51) Int. Cl.$^7$ .............................................. B29B 9/00
(52) U.S. Cl. .............................................. 264/7; 264/13
(58) Field of Search ........................................ 264/7, 13

(56) References Cited

U.S. PATENT DOCUMENTS 4,734,227 A * 3/1988 Smith ........................ 264/13
5,833,891 A * 11/1998 Subramaniam et al. ....... 264/12
6,056,791 A * 5/2000 Weidner et al. ........... 23/295 R

FOREIGN PATENT DOCUMENTS

| WO | 9521688 | 8/1995 |
| WO | 9615133 | 5/1996 |
| WO | 9816204 | 4/1998 |

* cited by examiner

Primary Examiner—Mary Lynn Theisen
(74) Attorney, Agent, or Firm—Webb Ziesenheim Logsdon Orkin & Hanson, P.C.

(57) ABSTRACT

In a process for producing a pulverulent product from a liquid substance or mixture of substances, the liquid substance or mixture of substances to be pulverized is first provided in a pressure vessel. A gas is then dissolved under elevated pressure in the liquid substance or mixture of substances. The resulting liquid/gas solution is then conducted out of the pressure vessel and to an expansion element, through which it is passed and rapidly expanded. Upstream of the expansion element, in the expansion element or downstream, in particular just downstream, of the expansion element, a solid pulverulent auxiliary is admixed. In this manner, a stable pulverulent product results from the solution or from the substance or mixture of substances.

20 Claims, 1 Drawing Sheet

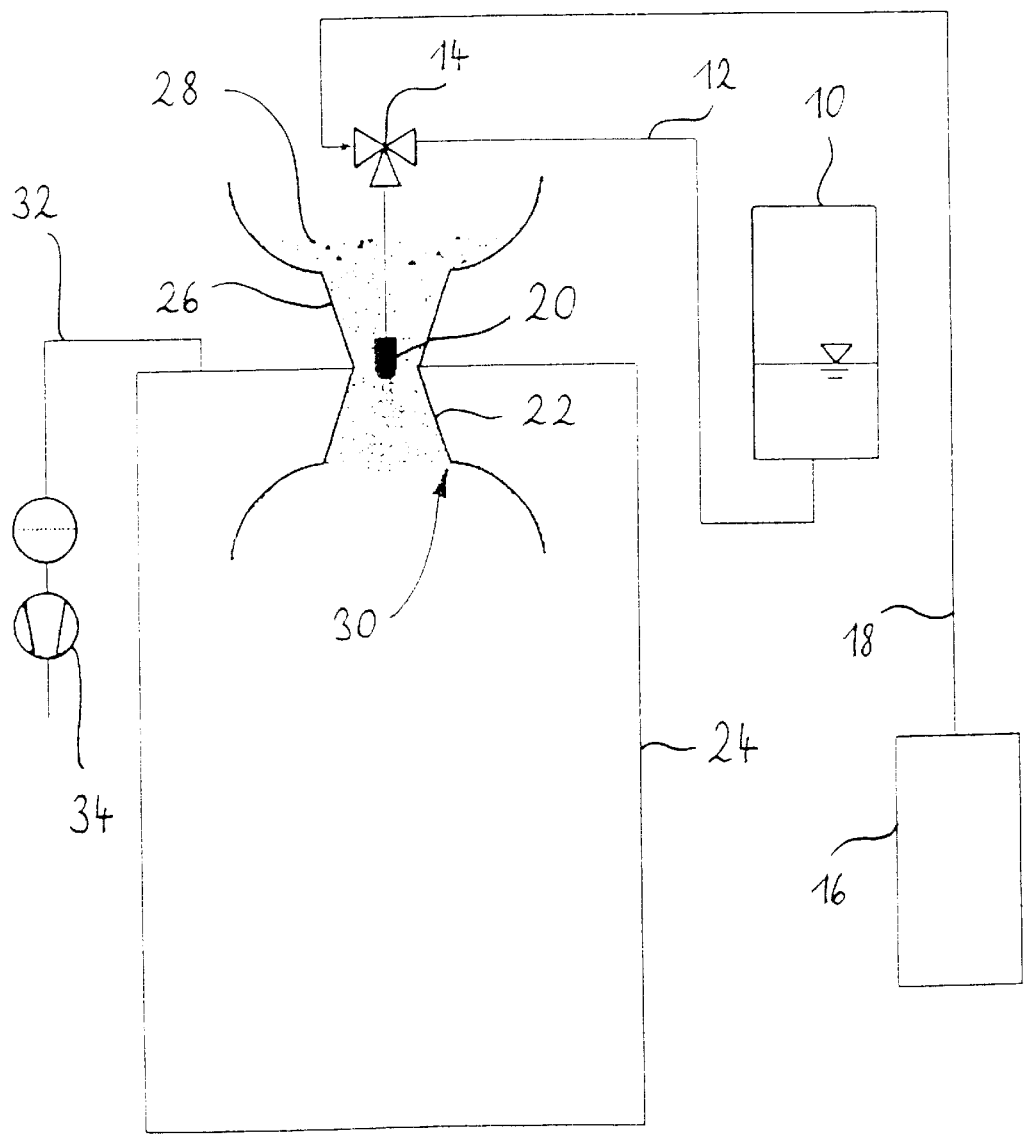

METHOD FOR PRODUCING A POWDER PRODUCT FROM A LIQUID SUBSTANCE OR MIXTURE OF SUBSTANCES

The invention relates to a process for producing a pulverulent product from a liquid substance or mixture of substances at ambient temperature. A process of this type is disclosed by WO 95/21688.

Pulverulent products are frequently preferred because of their simpler handling in comparison with liquids. In the usual case, for example, the transport and storage of a pulverulent product is less critical than that of a liquid. To produce powders, mechanical processes, such as grinding and agglomeration, and thermal processes, such as crystallization and spray-drying, are known. Substances which are pulverized by such classical processes generally have a melting point which is significantly above the ambient temperature (room temperature). This means that the physical state of these substances is not changed by the pulverization.

Substances whose melting point is beneath the usual ambient temperature cannot be pulverized until they have been solidified by cooling. Even after the pulverization, the solid state of such substances can only be retained with the use of complex cold chains. Another possibility for stabilizing substances which are liquid at usual ambient temperature is applying the substance to be stabilized to finely divided support particles. In this case the support particles are fluidized using a gas stream and the liquid substance to be stabilized is sprayed onto the fluidized support particles. By means of this process, which has become known as fluidized-bed coating, the support particles are coated with a thin film of the liquid substance to be stabilized. The mass ratio between the support and the substance stabilized in this way is determined by the dimensions and the shape of the support particles as well as by the coating thickness. The achievable active ingredient concentrations (active ingredient is taken to mean here the substance which is liquid at room temperature and is to be stabilized) are between 1% by weight and at most about 10% by weight, based on the finished coated support particles. Furthermore, a coating technique of this type can only be employed with certain material combinations in which the mutual wetting and adhesion forces permit the production of a coated support particle. A further restriction is given by the liquid to be stabilized: if its viscosity is too high, it cannot be sprayed, or can only be sprayed with great effort. In the case of some liquids, the sprayability can be improved by dilution with suitable solvents, but this means additional expense and, furthermore, reduces the active ingredient content in the finished stabilized product, quite apart from the fact that the use of many solvents is now undesirable from physiological and environmental aspects.

The previously mentioned process disclosed by WO 95/21688 makes it possible to produce pulverulent solids from liquids. The principle of the process is to dissolve a gas in the liquid to be pulverized under elevated pressure, preferably until a gas-saturated solution is obtained. In comparison with the pure liquid, a solution of this type has a number of favourable properties: thus, usually, the viscosity of this solution in comparison with the pure liquid at the same temperature is decreased by several orders of magnitude and the surface tension is also markedly reduced. The pressurized liquid/gas solution is then passed to an expansion element and there rapidly expanded. In the course of this, the gas present in the liquid/gas solution cools significantly, with great increase in volume, and separates from the liquid. This process leads to the formation of small solid particles which consist entirely of the substance which was previously liquid. The solid particles formed can be separated off by conventional processes and, if desired, can be fractionated.

Although this known process is an elegant and simple method of converting liquids into a pulverulent product, the resulting pulverulent product must still be cooled if the melting point of the processed substance is below the usual ambient temperature.

The object therefore underlying the invention is to provide a process by which substances or mixtures of substances which are liquid at room temperature or at ambient temperature can be stabilized in powder form, with the resulting powder form needing to be stable at room temperature or usual ambient temperature.

This object is achieved according to the invention, starting from the process mentioned at the outset, by means of the fact that a solid, pulverulent auxiliary is admixed to the liquid substance or mixture of substances to be pulverized or to the liquid/gas solution upstream of the expansion element, in the expansion element or downstream, in particular just downstream of the expansion element. In the process according to the invention surprisingly, even relatively small additions of auxiliary are sufficient to stabilize the pulverulent product formed on rapid expansion of the liquid/gas solution. In this process, less solid auxiliary is required the higher the melting temperature of the starting substance to be pulverized. Thus, by the process according to the invention, pulverulent products can be produced which have a high active ingredient content. This means that in the case of many substances or mixtures of substances a comparatively small amount of auxiliary, for example 1 to 90% by weight, preferably 10 to 80% by weight, and particularly preferably only 20 to 50% by weight, is sufficient for stabilizing the resulting powder form. Such high active ingredient concentrations could not be achieved by the processes known hitherto.

In the expansion of the liquid/gas solution, the temperature may fall below the solidification temperature of the substance or mixture of substances, but this is not absolutely necessary in order to obtain the desired pulverulent product. However, it has proved to be expedient, with a number of applications, during the expansion of the liquid/gas solution, to attain a temperature which is at least in the vicinity of the solidification temperature of the substance or mixture of substances.

As gas, in principle, use may be made of any gas which dissolves sufficiently in the liquid substance or mixture of substances to be pulverized. For example, as gas, use can be made of carbon dioxide, a hydrocarbon, in particular methane, ethane, propane, butane, ethene, propene, or a halogenated hydrocarbon, an ether, an inert gas, in particular nitrogen, helium or argon, a gaseous oxide, in particular dinitrogen oxide or sulphur dioxide and ammonia. A mixture of two or more of the abovementioned gases can also be used.

The elevated pressure under which the gas is dissolved in the liquid substance or mixture of substances can be in the range from 5 bar to 800 bar, but preferably the pressure is in the range from 10 bar to 350 bar, and particularly preferably in the range from 20 bar to 250 bar.

Preferably, the dissolution of the gas in the liquid substance or mixture of substances is accelerated by mixing the gas with the liquid substance or mixture of substances. This mixing can be achieved, for example, by shaking or rolling the pressure vessel into which the liquid to be pulverized has been introduced. Alternatively, the solution formed in the pressure vessel can be stirred by means of an agitator. Yet another possibility for achieving good mixture of the liquid to be pulverized with the gas is to recirculate the liquid phase present in the pressure vessel and/or the gas phase, i.e. to pump it out of the pressure vessel and to feed it back to the pressure vessel in the area of the other respective phase. Yet another possibility is the use of a static mixer. Obviously, the abovementioned procedures can also be combined.

The process according to the invention functions in principle with any solid pulverulent auxiliary. However, those which are particularly suitable are auxiliaries having as small a particle size as possible, for which reason, according to a preferred embodiment of the process according to the invention, the particle size is less than 100 $\mu$m and, in particular, less than 50 $\mu$m. Auxiliaries which have a porous inner structure, whose internal surface area is therefore as large as possible, are particularly well suited for use in the process according to the invention. Examples of substances having a large internal surface area which may be mentioned here are zeolites and activated carbon. In general, a suitable auxiliary is selected according to technical, physiological and also, if appropriate, according to food-law aspects. Without any claim as to completeness, possible auxiliaries which may be mentioned here are starch, modified starch, common salt, sugar, proteins, gelatin, titanium dioxide, magnesium stearate, polyglycols, highly disperse silicon dioxide, silicic acid, bentonite, lime, glutamate, emulsifiers, in particular phospholipids or partial glycerides, fats, cellulose and cellulose derivatives, polylactic acid, waxes, dextrin, kaolin, thickeners, in particular alginates or pectin, very finely ground plant components or a mixture of two or more of the abovementioned substances each of which must be present in powder form.

Depending on the liquid substance or mixture of substances to be pulverized, certain auxiliaries are suitable for use in the process according to the invention: for example, phospholipids are highly suitable in principle as an auxiliary for stabilizing the desired powder form. Furthermore, phospholipids are natural highly effective emulsifiers both for water-in-oil emulsions and for oil-in-water emulsions. Phospho-lipids therefore improve the water dispersibility of oil-soluble substances and the oil-dispersibility of water-soluble substances. They are therefore used as auxiliary, in particular, if these additional properties are of relevance. Poly-ethylene glycol-s, highly disperse silicon dioxide, starch, modified starch and magnesium stearate are water-soluble or readily dispersible and are solubilizers for water-insoluble substances. The use of these substances as an auxiliary in the process according to the invention therefore not only stabilizes, as desired, the powder form, but simultaneously improves the water dispersibility or water solubility of oil-soluble substances or mixtures of substances.

In the process according to the invention, the auxiliary concentration, based on the total amount of liquid substance or mixture of substances and auxiliary, is to be as low as possible. Particularly preferably, the auxiliary concentration is therefore only up to 25% by weight. If auxiliary concentrations up to 25% by weight are not sufficient to stabilize the previously liquid pulverized substance, preferably, up to 50% by weight auxiliary concentration can also be used in the process according to the invention. In the case of some liquid substances or mixtures of substances to be pulverized, it may be necessary to choose the auxiliary concentration even higher, for instance up to 90% by weight. Even this relatively high auxiliary concentration still leads to active ingredient contents which are markedly above the active ingredient contents which are achievable by conventional processes.

As expansion element, use can be made in the process according to the invention of any apparatus which enables sufficiently rapid expansion of the liquid/gas solution. Preferably, as expansion element, use is made of a nozzle, a diffuser, a capillary, an orifice plate, a valve or a combination of the abovementioned expansion elements.

It is important in the process according to the invention that the added solid pulverulent auxiliary is mixed with the liquid/gas solution or—depending on where the pulverulent auxiliary is fed—with the substance or mixture of substances to be pulverized. If mixing is inadequate, some of the resulting pulverulent product may not be sufficiently stabilized and later melts or fuses together at room temperature or at usual ambient temperature.

To achieve good mixing of the auxiliary with the liquid/gas solution or with the substance or mixture of substances to be pulverized, various possible methods are available. Thus, the pulverulent auxiliary can be added, for example, at the point where the liquid/gas solution exits from the expansion element, that is at or just upstream of the expansion point. The auxiliary is then entrained in the free jet forming downstream of the expansion point, the vigorous and rapid volume expansion of the gas present in the liquid/gas solution ensuring an extremely intensive vortexing and mixing of the auxiliary with the substance or mixture of substances to be pulverized.

According to another embodiment of the process according to the invention, the auxiliary is fed in such a manner that it surrounds in the form of a ring the mass stream exiting from the expansion element in the area of the outlet point. In other words: the auxiliary is added—for example by a ring-shaped nozzle—around the free jet exiting from the expansion element, so that the free jet is in any case initially surrounded by the auxiliary. The turbulence occurring on exit of the free jet from the expansion element ensures good mixing of the auxiliary with the fine spray of the substance or mixture of substances to be pulverized. Surrounding the free jet with the auxiliary in addition ensures that, just after the exit from the expansion element, any liquid droplets still present cannot be deposited on a surrounding wall, but are entrained. According to a further development of the process according to the invention, the mass stream exiting from the expansion element and the auxiliary are conducted to a type of diffuser, by which the divergence of the free jet can be controlled. The diffuser can additionally have one or more vortex-shedding edges in order to effect a still more intensive mixing between the free jet and the auxiliary by the turbulence formed there.

In preferred embodiments of the process according to the invention, the liquid/gas solution is expanded into a spray tower. The auxiliary to be admixed can then, for example, be transported by means of pneumatic transport into the spray tower and added at the desired point. Alternatively, the cold powder can be taken off from the spray tower and mixed in a separate mixer with precooled pulverulent auxiliary at a temperature beneath the melting point of the substance or mixture of substances to be pulverized.

In preferred embodiments of the process according to the invention, in addition to the gas which is already dissolved in the substance or mixture of substances to be pulverized, further gas is added in the area of the expansion element, which gas can be termed so-called excess gas. By means of this excess gas, the temperature reached in the expansion process may be set more independently. It is not necessary for the liquid/gas solution to be essentially saturated with the gas, nor, for example, need a relatively high pressure be chosen in order to achieve a gas concentration in the liquid which is sufficiently high for the desired cooling. Rather, the desired cooling in the area of the expansion point can substantially be effected by the rapid expansion of the additionally fed excess gas. Furthermore, there is the possibility of selecting as excess gas a gas which is different from the gas dissolved in the liquid. For example, the excess gas can be selected with regard to a temperature decrease as great as possible, whereas the gas to be dissolved in the liquid is specified according to other aspects. In addition to improved cooling in the area of the expansion point, the excess gas also leads to a still better mixing or vortexing after the exit of the mass stream from the expansion element and thus to still smaller powder particles.

Various possibilities exist with respect to feeding the excess gas. According to one embodiment of the process according to the invention, the excess gas is fed into the liquid/gas solution between the pressure vessel and the expansion element, in particular just upstream of the expansion point. In this case, for improved mixing with the liquid/gas solution, a static mixer can be used, for example.

According to another embodiment, in the expansion element, by means of a two-component nozzle, the liquid/gas solution and additionally supplied excess gas are expanded together with one another. In this embodiment, the excess gas is therefore not added to the liquid/gas solution, but is fed directly to the expansion point, so that the liquid/gas solution and the pure excess gas are expanded simultaneously. The two-component nozzle can be, for example, of a type such that the liquid/gas solution exits through a central channel, whereas the excess gas exits through a ring channel which coaxially surrounds the central channel.

According to yet another embodiment, the excess gas together with the solid pulverulent auxiliary is fed to the solution or the substance or mixture of substances.

When the substance or mixture of substances to be pulverized is mentioned above, this is taken to mean that the liquid to be pulverized need not be a pure substance, but it can perfectly well be a mixture or solution of various liquids or substances, the liquids or substances being able to be either organic or inorganic liquids or substances. Furthermore, a further substance may be added to a liquid pure substance, which further substance affects the properties of the resulting pulverulent end product in a desired manner. For example, an emulsifier can be added to a water-insoluble liquid to be pulverized in order in this manner to achieve improved water dispersibility of the pulverulent end product. The liquid substance to be pulverized or the mixture of substances can also be a suspension.

With reference to the single figure, an apparatus is described in more detail below which can be used with advantage for carrying out the process according to the invention.

The figure shows, as pressure vessel, an autoclave 10 into which the liquid substance to be pulverized or the mixture of substances is charged. By suitable measures, for example by agitating the autoclave 10 or the autoclave contents, a selected gas is then dissolved under pressure in the liquid introduced. The selected gas is fed in a conventional manner and the feed is not shown in the figure. To accelerate the dissolution of gas in the liquid to be pulverized, the liquid and the gas to be dissolved therein can be conducted cocurrently through a static mixer and can then be introduced into the autoclave 10. Depending on the type of gas selected, and depending on the pressure selected and on the temperature, gas concentrations in the liquid phase between 1 and 90% by weight, preferably from 5 to 50% by weight, and in particular from 10 to 40% by weight, can be achieved. The temperature is expediently in the range of room temperature or ambient temperature, but in the case of high-viscosity substances or mixtures of substances a higher temperature can be necessary. It is essential that the substance or the mixture of substances to be pulverized is present as liquid or suspension in the pressure vessel.

The liquid/gas solution present in the autoclave 10 after dissolution of the gas is fed via a line 12 to a three-way valve 14. From a gas vessel 16, additional gas, so-called excess gas, is fed via a line 18 to the three-way valve 14. The excess gas can be a gas other than the gas dissolved in the liquid.

From the three-way valve 14, the liquid/gas solution and the excess gas fed are passed to an expansion element which is here a high-pressure nozzle 20. Between the high-pressure nozzle 20 and the three-way valve 14, an additional static mixer can be provided in order to improve mixing of the excess gas into the liquid/gas solution.

The high-pressure nozzle 20 is arranged at the narrowest point of a diffuser 22 which is fixed in the top cover of a spray tower 24. Via a funnel 26 connected to the diffuser 22, a solid pulverulent auxiliary 28 is added continuously as long as the liquid/gas solution and the excess gas flow out of the high-pressure nozzle 20. Between the high-pressure nozzle 20 and the inner wall of the funnel 26 or the diffuser 22 is formed an initially contracting and then expanding again ring gap through which flows the added auxiliary 28. The auxiliary therefore annularly surrounds the mass stream flowing out of the high-pressure nozzle 20. The auxiliary 28 can be transported into the funnel 26 by known methods, for example by pneumatic transport, by shaking rails, by means of a screw conveyor, a starwheel feeder or the like.

The great increase in volume of the gas present in the liquid/gas solution and of the additionally fed excess gas after the exit from the high-pressure nozzle 20 leads to high turbulence and thus to good mixing of the auxiliary with the mass stream exiting from the high-pressure nozzle 20. In the exemplary embodiment shown, a vortex-shedding edge 30 present in the diffuser further increases the turbulence.

The intense cooling which is due to the expansion of the gas dissolved in the liquid and of the excess gas ensures, together with the high turbulence mentioned, mixing with the auxiliary which is so rapid and intensive that the pulverulent final product wanted is obtained even at a spray tower height of only 1 m. The powder collects in the lower part of the spray tower 24 and can be withdrawn in a conventional manner.

The gas dissolved in the liquid and the excess gas separate, downstream of the exit from the high-pressure nozzle 20, from the substance or mixture of substances to be pulverized. In the exemplary embodiment shown, the gas released in this manner is taken off in the upper area of the spray tower 24 by a line 32. The calming zone present between the diffuser 22 and the spray tower inner wall avoids a discharge of fine particles through the line 32. Any fine fraction of pulverized product which may nevertheless be present in the gas removed by suction may still be separated off from the gas stream upstream of a suction fan designated by 34 in a conventional manner, e.g. by means of a cyclone which is not depicted here.

Some examples of applications of the process according to the invention will now be specified, some of which arose with use of the apparatus described above.

EXAMPLE 1

3 kg of a low-water and low-aroma homogenized liquid pigment concentrate (colour index 130,000), which had been produced from paprika by extraction with hexane, were introduced into the autoclave 10 having a volume of 5 1. Carbon dioxide, at a pressure of 125 bar and a temperature of 32° C. was then run through the liquid for 90 min from bottom to top, in order to saturate the liquid pigment concentrate with the gas, at least approximately, under the specified conditions.

The carbon dioxide supply was then terminated, the spray line 12 was opened and the resulting gas-containing solution was expanded through a nozzle 20 having an opening diameter of 0.3 mm which was integrated into the top cover of the spray tower 24. By feeding additional carbon dioxide to the gas-containing solution just upstream of the expansion point, the temperature in the spray tower was set to −25° C. In the annular space (see diagram) around the nozzle 20, highly disperse silicon dioxide was added during the spraying operation. After a spraying time of 1 min, 100 g of a homogeneous powder were taken off from the spray tower. The content of auxiliary (silicon dioxide) was 30% by weight, and thus that of the active ingredient (pigment concentrate) was 70% by weight. The powder form of the resulting product was retained, even on warming to a temperature of 35° C. This is notable to the extent that the starting pigment concentrate is liquid at such a temperature and even on cooling to −18° C., still has a creamy consistency. By means of the process described, therefore, stabilization of the powder form is achieved at temperatures which are more than 50° C. above the solidification temperature of the substance to be pulverized in the present example.

EXAMPLE 2

Carbon dioxide at 250 bar and 50° C. was run for 3 hours through the paprika pigment concentrate described in Example 1. The resulting gas-containing solution was atomized as in Example 1. Feed of carbon dioxide just upstream of the expansion point set the temperature in the spray tower to −30° C. Pulverulent polyethylene glycol was added as auxiliary as described in Example 1. After completion of the experiment, 200 g of powder having an auxiliary content (polyethylene glycol) of 70% by weight could be withdrawn from the spray tower. The powder form was retained even on warming to 25° C.

EXAMPLE 3

3 kg of a low-water and low-aroma homogenized pigment concentrate (colour index 80,000) which had been produced from paprika by extraction with carbon dioxide were placed in the autoclave 10 having a volume of 5 1. Carbon dioxide was passed through the liquid from bottom to top at a pressure of 125 bar and a temperature of 32° C. for 90 min. The carbon dioxide feed was then terminated and the spray line was opened.

The gas-containing solution was expanded by a nozzle 20 integrated into the top cover of the spray tower 24 having an opening diameter of 0.5 mm. During expansion of the gas-saturated solution, a spray tower temperature of 0° C. was established. During the spraying operation, highly disperse silicon dioxide was metered into the annular space (see diagram) around the nozzle 20. After a spraying time of 1 min, 900 g of a homogeneous powder were withdrawn from the spray tower. The silicon dioxide content was 35% by weight. The powder form was retained even on warming to a temperature of 35° C.

EXAMPLE 4

42 kg of a commercial paprika extract (colour index 130,000) which had been produced by extraction of paprika powder with hexane were introduced into an autoclave having a volume of 400 l. Carbon dioxide was dissolved in the extract at a pressure of 250 bar and a temperature of 50° C. The pigment concentrate was then sprayed through a nozzle having an opening diameter of 0.8 mm. During the spraying operation, highly disperse silicon dioxide was metered in by a double diaphragm pump operated by compressed air. The auxiliary was added at a point in the area of the nozzle opening.

55.3 kg of powder having a content of highly disperse silicon dioxide of approximately 24% by weight were produced in 38 min at a temperature in the spray tower of −10° C. The powder remained free-flowing even at room temperature.

EXAMPLE 5

300 g of an aroma oil which had been produced from rosemary were introduced into an autoclave having a volume of 1 l. Carbon dioxide was dissolved in the liquid at a pressure of 100 bar and room temperature. The gas-containing solution was expanded into a spray tower through a nozzle having an opening diameter of 0.3 mm. The temperature in the spray tower was −5° C. As auxiliary, highly disperse silicon dioxide was added to the free jet. A pulverulent solid having an auxiliary content (silicon dioxide) of 25% by weight is obtained. The active ingredient content (rosemary) of the resulting powder was thus 75% by weight.

EXAMPLE 6

250 g of an aroma oil which had been produced from rosemary were introduced into an autoclave having a volume of 1 l. Carbon dioxide was dissolved in the liquid at a pressure of 150 bar and a temperature of 33° C. The gas-containing solution was fed via a spray line heated to 60° C. to a nozzle having an opening diameter of 0.3 mm and expanded into a spray tower. By metering additional carbon dioxide, a temperature of −12° C. was established in the spray tower. During the expansion, Palatinit (Isomalt) was added. A pulverulent product having a Palatinit content of 87% by weight is obtained.

EXAMPLE 7

300 g of an aroma oil which had been produced from rosemary extract were introduced into an autoclave having a volume of 1 l. Carbon dioxide was dissolved in the liquid at a pressure of 150 bar and a temperature of 19° C. The gas-containing solution was fed via a spray line of the same temperature to a nozzle having an opening diameter of 0.3 mm and expanded into a spray tower. By metering additional carbon dioxide, a temperature of −18° C. was established in the spray tower. During the expansion, a mixture of 80% by weight Palatinit (Isomalt) and 20% by weight highly disperse silicon dioxide was added. A pulverulent product having an auxiliary (Palatinit+silicon dioxide) content of 50% by weight is obtained.

EXAMPLE 8

280 g of a liquid preparation of a pepper extract were introduced into an autoclave having a volume of 1 l. The preparation has a piperine content of 40% by weight, an aroma oil content of 10% by weight and an emulsifier content of 15% by weight. Carbon dioxide was dissolved in the liquid at a pressure of 70 bar and a temperature of 42° C. The gas-containing solution was fed via a spray line of the same temperature to a nozzle having an opening diameter of 0.3 mm and expanded into a spray tower. By metering additional carbon dioxide, a temperature of −14° C. was established in the spray tower. During the expansion, highly disperse silicon dioxide was added. A pulverulent free-flowing product having an auxiliary (silicon dioxide) content of 39% by weight is obtained.

EXAMPLE 9

270 g of a liquid preparation of a pepper extract were introduced into an autoclave having a volume of 1 l. The preparation has a piperine content of 40% by weight, an aroma oil content of less than 5% by weight and an emulsifier content of 15% by weight. Carbon dioxide was dissolved in the liquid at a pressure of 110 bar and a temperature of 42° C. The gas-containing solution was fed via a spray line of the same temperature to a nozzle having an opening diameter of 0.3 mm and expanded into a spray tower. By metering additional carbon dioxide, a temperature of −4° C. was established in the spray tower. During the expansion, highly disperse silicon dioxide was added. A pulverulent free-flowing product having an auxiliary (silicon dioxide) content of 21% by weight is obtained.

EXAMPLE 10

290 g of a celery extract which is mobile at room temperature were introduced into an autoclave having a volume of 1 l. Carbon dioxide was dissolved in the liquid at a pressure of 160 bar and a temperature of 42° C. The gas-containing solution was fed via a spray line of the same temperature to a nozzle having an opening diameter of 0.3 mm and expanded into a spray tower. By metering additional carbon dioxide, a temperature of 5° C. was established in the spray tower. During the expansion, highly disperse silicon dioxide was added. A pulverulent free-flowing product having an auxiliary (silicon dioxide) content of 35% by weight is obtained.

What is claimed is:

1. A process for producing a pulverulent product from at least one substance at room temperature, having the steps of:
   providing, in a pressure vessel, the at least one substance to be pulverized;
   dissolving a gas in the at least one substance under elevated pressure to produce a liquid/gas solution;
   conducting the liquid/gas solution out of the pressure vessel to an expansion element; and
   passing the liquid/gas solution through the expansion element for rapid expansion of the solution, wherein a solid, pulverulent auxiliary is admixed to an ingredient selected from the group consisting of the at least one substance and the liquid/gas solution.

2. The process according to claim 1, wherein the expansion process taking place during passage of the liquid/gas solution through the expansion element is carried out in such a manner that the temperature roughly attains or falls below the solidification temperature of the at least one substance.

3. The process according to claim 1, wherein gas is dissolved in the at least one substance until the at least one substance is essentially saturated with the gas.

4. The process according to claim 1, wherein the gas is at least one gas selected from the group consisting of carbon dioxide, hydrocarbons, halogenated hydrocarbons, ethers, inert gases, gaseous oxides and ammonia.

5. The process according to claim 1, wherein the elevated pressure under which the gas is dissolved in the at least one liquid substance is in the range from 5 bar to 800 bar.

6. The process according to claim 1, wherein the dissolution of the gas in the at least one substance is accelerated by mixing the gas with the at least one substance.

7. The process according to claim 6, wherein the gas is mixed with the at least one substance by at least one technique selected from the group consisting of static mixing, shaking the pressure vessel, rolling the pressure vessel, stirring the solution forming in the pressure vessel, recirculating the liquid phase present in the pressure vessel and recirculating the gas phase present in the pressure vessel.

8. The process according to claim 1, wherein the particle size of the pulverulent auxiliary is less than 100 μm.

9. The process according to claim 1, wherein at least one ingredient is selected from the group consisting of starch, modified starch, common salt, sugar, proteins, gelatin, titanium dioxide, magnesium stearate, polyglycols, highly dispersed silicon dioxide, silicic acid, bentonite, lime, glutamate, emulsifiers, phospho-lipids, partial glycerides, fats, cellulose, cellulose derivatives, polylactic acid, waxes, dextrin, kaolin, zeolites, thickeners, alginates, pectin, activated carbon and very finely ground plant components.

10. The process according to claim 1, wherein the auxiliary concentration, based on the total amount of the at least one substance and auxiliary, is between 1% by weight and 90% by weight.

11. The process according to claim 1, wherein the expansion element comprises at least one device selected from the group consisting of a nozzle, a diffuser, a capillary, an orifice plate and a valve.

12. The process according to claim 1, wherein the auxiliary is fed to the liquid/gas solution at the point where the liquid/gas solution exits from the expansion element.

13. The process according to claim 1, wherein the solution is expanded into a spray tower.

14. The process according to claim 1, wherein gas is additionally fed into the liquid/gas solution between the pressure vessel and the expansion element.

15. The process according to claim 1, wherein the liquid/gas solution and additionally supplied gas are expanded together with one another in the expansion element by means of a two-component nozzle.

16. The process according to claim 1, wherein additional gas is also fed together with the feed of the solid pulverulent auxiliary to an ingredient selected from the group consisting of the at least one substance and the liquid/gas solution.

17. The process according to claim 1, wherein the solid, pulverulent auxiliary is admixed to the at least one substance upstream of the expansion element.

18. The process according to claim 1, wherein the solid, pulverulent auxiliary is admixed to the liquid/gas solution upstream of the expansion element.

19. The process according to claim 1, wherein the solid, pulverulent auxiliary is admixed to the liquid/gas solution in the expansion element.

20. The process according to claim 1, wherein the solid, pulverulent auxiliary is admixed to the liquid/gas solution downstream of the expansion element.

* * * * *